United States Patent [19]

Morita et al.

[11] Patent Number: 5,034,230
[45] Date of Patent: Jul. 23, 1991

[54] ANTI-ALLERGIC OPHTHALMICS

[75] Inventors: Takakazu Morita, Toyonaka; Tadashi Iso, Kawachinagano; Youichi Kawashima, Kyoto; Mitsushi Hikida, Takatsuki, all of Japan

[73] Assignee: Santen Pharmaceutical Co., Ltd., Osaka, Japan

[21] Appl. No.: 392,922

[22] PCT Filed: Dec. 23, 1988

[86] PCT No.: PCT/JP88/01296
§ 371 Date: Jul. 28, 1989
§ 102(e) Date: Jul. 28, 1989

[87] PCT Pub. No.: WO89/06130
PCT Pub. Date: Jul. 13, 1989

[30] Foreign Application Priority Data
Dec. 25, 1987 [JP] Japan ................ 62-331025

[51] Int. Cl.$^5$ ............................ A61F 2/00; A61K 9/08
[52] U.S. Cl. ............................. 424/427; 424/428; 424/659; 424/660; 514/914; 514/269
[58] Field of Search ............... 514/269, 914; 424/427, 424/659, 660, 428

[56] References Cited
U.S. PATENT DOCUMENTS
4,122,274 10/1978 Juby ............................ 544/116

FOREIGN PATENT DOCUMENTS
60-50197 11/1985 Japan .

Primary Examiner—Thurman K. Page
Assistant Examiner—James M. Spear
Attorney, Agent, or Firm—Frishauf, Holtz, Goodman & Woodward

[57] ABSTRACT

This invention relates to low irritative ophthalmics containing the compound of the formula or salts thereof which are useful for treatment of anti-allergic eye diseases such as allergic conjunctivitis

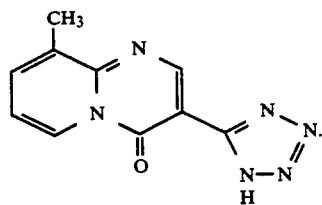

22 Claims, No Drawings

ANTI-ALLERGIC OPHTHALMICS

FIELD OF THE INVENTION

This invention offers ophthalmics which are useful for treatment of allergic eye diseases such as allergic conjunctivitis.

BACKGROUND OF THE INVENTION

Japanese Patent Publication ( Publication No. Sho 60-50197 ) discloses that the compound of the formula [I] and salts thereof ( hereinafter called as Compound [I]) are excellent anti-allergic drugs.

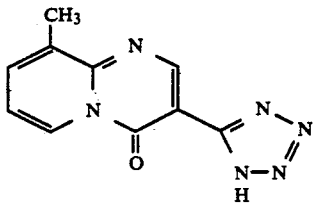

But, ophthalmic application of Compound [I] has not been studied, so, it is necessary to examine preparation methods of ophthalmic formulations and study the effect on allergic eye diseases.

As the result of our precise studies on preparation methods of ophthalmic formulations and the effect on allergic eye diseases, we found that Compound [I] has an excellent anti-allergic effect in eyes and has a possibility to be applied to stable and low irritative ophthalmics.

DISCLOSURE OF THE INVENTION

This invention relates to the anti-allergic ophthalmics containing the compound of the formula [I] or salts thereof ( hereinafter called as Compound [I]) as a main ingredient.

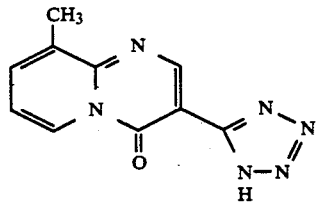

Examples of the salts of the compound [I] are metal salts such as potassium, sodium, calcium and magnesium and organic amine salts.

Compound [I] is already known to have an excellent anti-allergic effect However, the application to ophthalmics and its effect on allergic eye diseases have not been known.

Topical diseases such as eye diseases are efficiently treated by topical application of a drug and it is necessary to study a topical application of oral drug to ophthalmics Especially, the potassium salt of Compound[I], that is 9-methyl-3-(1H-tetrazole-5-yl)-4H-pyrido[1,2-a]pyrimidine-4-one potassium salt ( hereinafter called as Compound A ), is an excellent anti-allergic drug, so we studied mainly an application of the potassium salt to ophthalmics.

Important factors for ophthalmics are not only to have excellent efficacy, but also low irritation because ophthalmics are administered directly to the eye, which is a highly sensitive organ.

Particularly, patients with allergic diseases complain of a strong pain in the eye, so less irritative ophthalmics are desired to treat such patients As the result of the experiment using eye drops of Compound A as one of the examples, the details of which are described later in the article of the irritation test, we found that the eye drops cause little eye irritation and the ophthalmics of this invention are well applicable to anti-allergic ophthalmics.

Furthermore, in the case of eye drops, stability in solution is required, which is different from an oral drug, because the ingredients should be dissolved. We examined the stability of the eye drops of compound A. As the result of a preservation test during 6 months in the condition at 40° C. and 75% of relative humidity, a notable change was not observed and the eye drops proved to have good stability.

These properties cannot be presumed from the properties of oral preparations and can be found only from the application study to ophthalmics.

We examined the efficacy of ophthalmics, which is the most important property, and found that Compound A showed strong anti-allergic effect by topical application, the details of which and described later in the disclosure of the pharmacological test using eye drops of Compound A, and the ophthalmics of this invention were very useful for treatment of allergic eye diseases, such as allergic conjunctivitis.

Furthermore, to apply a medical substance to eye drops, the solubility of the substance is an important factor.

If a substance is easily soluble in water, any particular consideration is not necessary.

But, if a medical substance is hardly soluble in water, or if a substance, once dissolved in water, is readily crystallized while storing, many kinds of studies are required to formulate such substance in eye drops.

Compound A, which is an excellent anti-allergic drug, is a water soluble substance, but, readily precipitates as crystals after being dissolved in water. So, such problem about soluability has to be solved to formulate Compound A in eye drops.

A method using a solubilizer such as polyvinyl alcohol is considered first. However, the problem mentioned above can not be solved and another idea is required. Furthermore, in the case of eye drops, when a concentration of potassium is raised, there is a fear of causing corneal damage. So, particular consideration is required to apply such substance to ophthalmics.

When dosage frequency is not high, the potassium concentration is not an important problem. But, when continuous administration of the ophthalmics is required to treat eye diseases, it is important to lower the potassium concentration.

As the result of our intensive studies to solve such problems, we found that the problems could be solved immediately by using a sodium phosphate buffer or borate buffer.

We found that especially superior eye drops could be prepared by using a combination of disodium hydrogen phosphate and sodium dihydrogen phosphate, disodium hydrogen phosphate and potassium dihydrogen phosphate, boric acid and sodium borate or boric acid and monoethanolamine.

The combination amount and ratio of the buffer depend on the concentration of Compound A, however, when the concentration of Compound A is 0.01–1%, the following are preferable combinations.

Disodium hydrogen phosphate and sodium dihydrogen phosphate are 0.1–2% and 0.002–1% respectively Disodium hydrogen phosphate and potassium dihydrogen phosphate are 0.1–1% and 0.002–0.7% respectively. Boric acid and sodium borate are 0.3–2% and 0.3–1% respectively. Boric acid and monoethanolamine are 0.3–2% and 0.1–1% respectively.

We explained eye drops of Compound A in detail. However, this invention should not be restricted to eye drops, but should include all dosage forms such as suspensions and eye ointments which can be administered topically. The ophthalmics can be prepared by combining additives required according to the dosage forms.

Examples of additives usually combined in ophthalmics are tonicity agents such as sodium chloride, potassium chloride and concentrated glycerin, stabilizers such as sodium sulfite and disodium edetate, preservatives such as benzalkonium chloride, surfactants such as polysorbate 80 and polyoxyethylene hydrogenated castor oil, pH adjusting agents such as sodium hydroxide, potassium hydroxide and hydrochloric acid and eye ointment bases such as vaseline and liquid paraffin.

The concentration of Compound [I] in ophthalmics can be defined in the range of effective dose, but preferably 0.01–1%.

The pH value of the ophthalmics of this invention can be adjusted according to the range acceptable in ophthalmics, but in eye drops of Compound A, the pH is preferably 7–9.

The typical preparation method of the ophthalmics of this invention is that Compound[I] is added to sterile purified water or an eye ointment base and formulated by adding a tonicity agent, buffering agent, stabilizer, preservatives, surfactant, pH adjusting agent, etc.

BEST MODE TO MAKE THE INVENTION

Example 1

Formulation A

| Compound A | 0.3 g |
|---|---|
| sodium dihydrogen phosphate | 0.01 g |
| disodium hydrogen phosphate | 0.35 g |
| concentrated glycerin | 2.0 g |
| benzalkonium chloride | 0.005 g |
| sterile purified water | q.s. |
| total | 100 ml |

Preparation method

Sodium dihydrogen phosphate, disodium hydrogen phosphate, concentrated glycerin and benzalkonium chloride were dissolved in 80 ml of sterile purified water and then Compound A was added to the solution. After dissolving Compound A, sterile purified water was added to adjust the total volume to 100 ml.

Eye drops of the formulation B–E were prepared by the similar method as Example 1.

Formulation B

| Compound A | 0.05 g |
|---|---|
| sodium dihydrogen phosphate | 0.04 g |
| disodium hydrogen phosphate | 1.4 g |
| potassium chloride | 0.7 g |
| benzalkonium chloride | 0.005 g |
| sterile purified water | q.s. |
| total | 100 ml |

Formulation C

| Compound A | 1.0 g |
|---|---|
| boric acid | 1.8 g |
| monoethanolamine | 0.6 g |
| sodium sulfite | 0.2 g |
| benzalkonium chloride | 0.005 g |
| sterile purified water | q.s. |
| total | 100 ml |

Formulation D

| Compound A | 0.01 g |
|---|---|
| boric acid | 0.81 g |
| sodium borate | 0.67 g |
| potassium chloride | 0.24 g |
| benzalkonium chloride | 0.005 g |
| sterile purified water | q.s. |
| total | 100 ml |

Formulation E

| Compound A | 0.1 g |
|---|---|
| sodium dihydrogen phosphate | 0.008 g |
| disodium hydrogen phosphate | 0.32 g |
| concentrated glycerin | 1.8 g |
| benzalkonium chloride | 0.005 g |
| sterile purified water | q.s. |
| total | 100 ml |

Example 2

Formulation F

| Compound A | 0.5 g |
|---|---|
| boric acid | 0.7 g |
| sodium chloride | 0.13 g |
| benzalkonium chloride | 0.005 g |
| potassium hydroxide | q.s. |
| sterile purified water | q.s. |
| total | 100 ml |

Preparation method

Boric acid, sodium chloride and benzalkonium chloride were dissolved in 80 ml of sterile purified water. Compound A was added to the solution, pH was adjusted to 8.5 with potassium hydroxide and sterile purified water was added to the solution to adjust the total volume to 100ml Eye drops of the formulations G–I were prepared by the similar method as Example 2.

Formulation G

| Compound A | 0.01 g |
|---|---|
| sodium dihydrogen phosphate | 0.73 g |
| disodium hydrogen phosphate | 0.71 g |
| benzalkonium chloride | 0.005 g |
| potassium chloride | 0.21 g |

-continued

| | |
|---|---|
| potassium hydroxide | q.s. |
| sterile purified water | q.s. |
| total | 100 ml |

Formulation H

| | |
|---|---|
| Compound A | 0.01 g |
| potassium dihydrogen phosphate | 0.6 g |
| disodium hydrogen phosphate | 0.3 g |
| benzalkonium chloride | 0.01 g |
| potassium chloride | 0.5 g |
| sodium hydroxide | q.s. |
| sterile purified water | q.s. |
| total | 100 ml |

Formulation I

| | |
|---|---|
| Compound A | 1.0 g |
| sodium dihydrogen phosphate | 0.3 g |
| disodium hydrogen phosphate | 0.15 g |
| concentrated glycerin | 1.4 g |
| benzalkonium chloride | 0.005 g |
| potassium hydroxide | q.s. |
| sterile purified water | q.s. |
| total | 100 ml |

PHARMACOLOGICAL TEST

The inhibition effect of an anaphylactic reaction is usually measured as an indication to examine an efficacy on allergic diseases.

We examined the inhibition effect of an anaphylactic reaction of ophthalmics of this invention, using a rat conjunctiva model in which a passive cutaneous anaphylactic reaction was induced. Sodium cromoglycate, which has been applied to anti-allergic ophthalmics, was used as a comparative drug.

Experimental Method

According to the method of ISO et. al. ( Ophthalmic Res., 12, 9 (1980) ), we examined the inhibition effects of test compounds on allergy of rat conjunctiva, using four times diluted antiserum ( PCA titer 1:32 ) prepared by Mota's method (Life Sci., 12, 917 (1963) ). Ten μl of eye drops, which was prepared by dissolving the test compound in saline and adjusted pH 7.5, was dropped 5 and 15 minutes before challenge of antigen.

Result

| test compound | concentration (%) | inhibition effect of anaphylactic reaction (%) |
|---|---|---|
| Compound A | 0.01 | 55.5 |
| Compound A | 0.1 | 88.5 |
| Compound A | 1.0 | 94.8 |
| Sodium cromoglycate | 1.0 | 9.5 |

The inhibition percent of the anaphylactic reaction of the eye drops of this invention is, even if the concentration of Compound A is low such as 0.01%, over 50%. In case of the eye drops containing 1.0% of Compound A, the inhibition percent was over 90%.

The anti-allergic effect of Compound A by topical application is superior to that of sodium cromoglycate.

The results prove the utility of the ophthalmics of this invention.

IRRITATION TEST

Measurement of blinking rate and Draze test using a rabbit are usually applied as the indicator to examine eye irritation caused by ophthalmics.

We examined the irritation, comparing the ophthalmics of this invention with its vehicle.

As one of the examples, the result using the ophthalmics of the Formulation I in Example 2 is shown below. Each blinking rate one minute after one drop application of the eye drops of the Formulation I or one drop of its vehicle is low, such as 0.8 times ( mean value of 5 rabbits ), and irritation by the medicament was not recognized.

After 10 times applications of the eye drops of the Formulation I or its vehicle, we scored according to the improved Draze method ( Fukui et. al., Gendai no Rinsyo 4, 277 (1970) ) and found no damage in either case. The results showed that the irritation of the ophthalmics of this invention was weak.

UTILITY IN AN INDUSTRY

This invention provides low irritative ophthalmics which are useful for treatment of allergic eye diseases such as allergic conjunctivitis.

What we claim is:

1. An anti-allergic ophthalmic solution comprising a potassium salt of a compound of the formula (I)

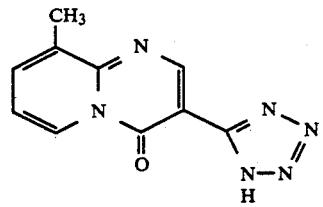

in a concentration from 0.01 to 1% and at least one buffer selected from the group consisting of disodium hydrogen phosphate, sodium dihydrogen phosphate, boric acid and sodium borate, either alone or in admixture with one or more pharmaceutically acceptable excipients.

2. An anti-allergic ophthalmic solution comprising a potassium salt of a compound of the formula (I)

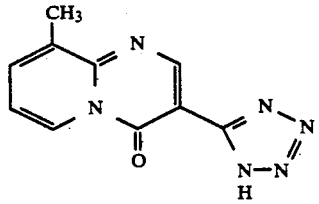

disodium hydrogen phosphate, sodium dihydrogen phosphate and optionally one or more pharmaceutically acceptable excipients, wherein the concentrations of the potassium salt of the compound of the formula (I), the disodium hydrogen phosphate and the sodium dihydrogen phosphate are 0.01 to 1%, 0.1 to 2% and 0.002 to 1%, respectively.

3. An anti-allergic ophthalmic solution comprising a potassium salt of a compound of the formula (I)

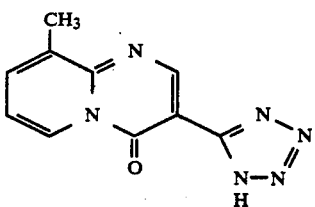

disodium hydrogen phosphate, potassium dihydrogen phosphate and optionally one or more pharmaceutically acceptable excipients, wherein the concentrations of the potassium salt of the compound of the formula (I), the disodium hydrogen phosphate, and the potassium dihydrogen phosphate are 0.01 to 1%, 0.1 to 1% and 0.002 to 0.7%, respectively.

4. An anti-allergic ophthalmic solution comprising a potassium salt of a compound of the formula (I)

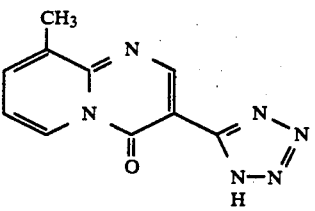

boric acid, sodium borate and optionally one or more pharmaceutically acceptable excipients, wherein the concentrations of the potassium salt of the compound of the formula (I), the boric acid and the sodium borate are 0.01 to 1%, 0.3 to 2% and 0.3 to 1%, respectively.

5. An anti-allergic ophthalmic solution comprising a potassium salt of a compound of the formula (I)

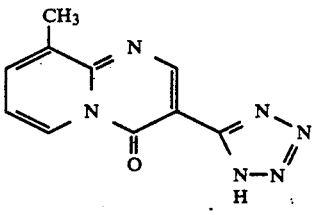

boric acid, monoethanolamine and optionally one or more pharmaceutically acceptable excipients, wherein the concentrations of the potassium salt of the compound of the formula (I), the boric acid and the monoethanolamine are 0.01 to 1%, 0.3 to 2% and 0.1 to 1%, respectively.

6. The anti-allergic ophthalmic solution according to claim 1, wherein the solution is in a dosage form and the dosage form comprises sterile aqueous eyedrops.

7. An anti-allergic ophthalmic solution prepared by dissolving a potassium salt of the compound of formula (I)

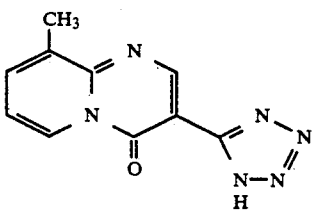

to provide said salt in a concentration from 0.01 to 1%, in sterile water containing disodium hydrogen phosphate, sodium dihydrogen phosphate and optionally one or more pharmaceutically acceptable excipients, wherein the concentrations of the disodium hydrogen phosphate and the sodium dihydrogen phosphate are 0.1 to 2% and 0.002 to 1%, respectively.

8. An anti-allergic ophthalmic solution prepared by dissolving a potassium salt of the compound of the formula (I)

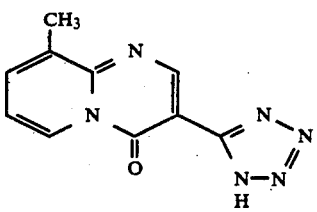

to provide said salt in a concentration from 0.01 to 1%, in sterile water containing disodium hydrogen phosphate, potassium dihydrogen phosphate and optionally one or more pharmaceutically acceptable excipients, wherein the concentrations of the disodium hydrogen phosphate and the potassium dihydrogen phosphate are 0.1 to 1% and 0.002 to 0.7%, respectively.

9. An anti-allergic ophthalmic solution prepared by dissolving a potassium salt of the compound of the formula (I).

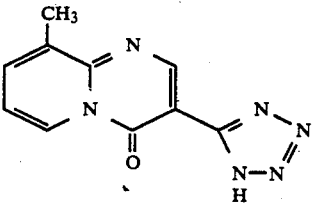

to provide salt in a concentration from 0.1 to 1%, in sterile water containing boric acid, sodium borate and optionally one or more pharmaceutically acceptable excipients, wherein the concentrations of the boric acid and the sodium borate are 0.3 to 2% and 0.3 to 1%, respectively.

10. An anti-allergic ophthalmic solution prepared by dissolving a potassium salt of the compound of the formula (I)

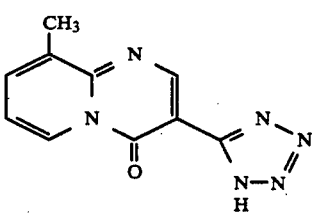

to provide said salt in a concentration from 0.01 to 1%, in a sterile water containing boric acid, monoethanolamine and optionally one or more pharmaceutically acceptable excipients, wherein the concentrations of the boric acid and the monoethanolamine are 0.3 to 2% and 0.1 to 1%, respectively.

11. A method of treatment of allergic eye diseases which comprises administering to a patient the anti-allergic ophthalmic solution according to claim 1 in an amount effective to treat an allergic eye disease.

12. The method according to claim 11, wherein the solution is topically administered to the eye of the patient in a dosage form and the dosage form comprises sterile aqueous eye drops.

13. A method of treatment of allergic eye diseases which comprises administering to a patient the anti-allergic ophthalmic solution according to claim 2 in an amount effective to treat an allergic eye disease.

14. A method of treatment of allergic eye diseases which comprises administering to a patient the anti-allergic ophthalmic solution according to claim 3 in an amount effective to treat an allergic eye disease.

15. A method of treatment of allergic eye diseases which comprises administering to a patient the anti-allergic ophthalmic solution according to claim 4 in an amount effective to treat an allergic eye disease.

16. A method of treatment of allergic eye diseases which comprises administering to a patient the anti-allergic ophthalmic solution according to claim 5 in an amount effective to treat an allergic eye disease.

17. The anti-allergic ophthalmic solution according to claim 1, wherein the concentration of the potassium salt of the compound of the formula (I) is about 0.1 to 1%.

18. The anti-allergic ophthalmic solution according to claim 2, wherein the concentration of the potassium salt of the compound of the formula (I) is about 0.1 to 1%.

19. The anti-allergic ophthalmic solution according to claim 3, wherein the concentration of the potassium salt of the compound of the formula (I) is about 0.1 to 1%.

20. The anti-allergic ophthalmic solution according to claim 4, wherein the concentration of the potassium salt of the compound of the formula (I) is about 0.1 to 1%.

21. The anti-allergic ophthalmic solution according to claim 5, wherein the concentration of the potassium salt of the compound of the formula (I) is about 0.1 to 1%.

22. A method of treatment of an allergic eye disease which comprises topically administering to a patient the anti-allergic ophthalmic solution according to claim 17 in an amount effective to treat an allergic eye disease.

* * * * *